(12) United States Patent
Yadav

(10) Patent No.: US 10,332,270 B2
(45) Date of Patent: Jun. 25, 2019

(54) PORTABLE SYSTEM FOR OBTAINING SPORTS INFORMATION

(71) Applicant: Chethan Yadav, Atlanta, GA (US)

(72) Inventor: Chethan Yadav, Atlanta, GA (US)

( * ) Notice: Subject to any disclaimer, the term of this patent is extended or adjusted under 35 U.S.C. 154(b) by 493 days.

(21) Appl. No.: 14/863,003

(22) Filed: Sep. 23, 2015

(65) Prior Publication Data

US 2017/0083758 A1 Mar. 23, 2017

(51) Int. Cl.
*G06K 9/00* (2006.01)
*A63B 24/00* (2006.01)
(Continued)

(52) U.S. Cl.
CPC .................. *G06T 7/60* (2013.01); *A61B 5/11* (2013.01); *A61B 5/1112* (2013.01); *G01S 19/52* (2013.01);
(Continued)

(58) Field of Classification Search
CPC ............ A63B 24/0062; A63B 2220/30; A63B 71/0622; A63B 2220/12; A63B 2220/40; A63B 2220/833; A63B 2225/50; A63B 2220/836; A63B 2225/20; A63B 2071/0625; A63B 2220/803; A63B 2220/20; G06F 3/0482; G06F 2203/04803; G06F 3/04842; G06F 3/04883; G06F 3/0488; G06F 3/0416; G06F 3/044; G06F 3/04817; G06F 3/04847; G06F 3/1423; G06F 1/1626; G06F 3/011; G06F 3/0412; G06F 3/04845; G11B 27/34; G11B 27/034; G11B 27/036; G11B 27/031; G11B 27/105; G11B 27/10; G11B 27/28; G11B 27/005; G11B 27/102; G11B 27/3027; G06T 7/20; G06T 2207/30221;
(Continued)

(56) References Cited

U.S. PATENT DOCUMENTS 6,375,579 B1 * 4/2002 Hart .................... A63B 69/3614
 473/131
6,582,328 B2 * 6/2003 Kuta ................... A63B 24/0021
 473/405

(Continued)

FOREIGN PATENT DOCUMENTS

WO 2014066779 A2 5/2014

OTHER PUBLICATIONS

International Search Report and Written Opinion issued in PCT/US2016/053222 dated Feb. 7, 2017.

*Primary Examiner* — Dave Czekaj
*Assistant Examiner* — Kehinde Abimbola
(74) *Attorney, Agent, or Firm* — Meunier Carlin & Curfman LLC

(57) ABSTRACT

A cost-effective, portable system is provided for obtaining and analyzing detailed sports information. The system may include, for example, a mobile device capable of calculating a distance between itself and a launch point of a ball, recording a video of the flight of the ball, analyzing the video to determine at least one flight characteristic, and determining, based on the at least one flight characteristic, an average speed of the ball during flight. The system may also include a sensor worn by a player and configured to wirelessly transmit various types of information to the mobile device for further processing.

15 Claims, 6 Drawing Sheets

US 10,332,270 B2
Page 2

(51) Int. Cl.
  *G06K 9/52* (2006.01)
  *G06T 7/20* (2017.01)
  *G06T 7/60* (2017.01)
  *H04N 7/18* (2006.01)
  *A61B 5/11* (2006.01)
  *G01S 19/52* (2010.01)
  *G16H 20/30* (2018.01)
  *A63B 69/38* (2006.01)
  *G01S 19/19* (2010.01)

(52) U.S. Cl.
  CPC ..... *G06K 9/00671* (2013.01); *G06K 9/00724* (2013.01); *G06K 9/00744* (2013.01); *G06T 7/20* (2013.01); *G16H 20/30* (2018.01); *A63B 69/38* (2013.01); *A63B 2207/02* (2013.01); *A63B 2220/12* (2013.01); *A63B 2220/17* (2013.01); *A63B 2220/20* (2013.01); *A63B 2220/30* (2013.01); *A63B 2220/35* (2013.01); *A63B 2220/53* (2013.01); *A63B 2220/806* (2013.01); *A63B 2225/50* (2013.01); *G01S 19/19* (2013.01); *G06T 2207/30224* (2013.01)

(58) Field of Classification Search
  CPC . G06T 2207/30241; G06T 2207/10016; G06T 7/251; G06T 13/40; G06T 19/006; G06T 2207/30; G06T 7/215
  See application file for complete search history.

(56) References Cited

U.S. PATENT DOCUMENTS

| | | | | |
|---|---|---|---|---|
| 7,255,647 | B2 * | 8/2007 | Zanzucchi | A63B 24/0003 473/156 |
| 7,292,711 | B2 * | 11/2007 | Kiraly | G06T 7/20 348/169 |
| 7,868,914 | B2 * | 1/2011 | Dengler | G06T 7/246 348/157 |
| 7,959,521 | B2 * | 6/2011 | Nusbaum | A63B 69/36 473/278 |
| 8,287,398 | B2 * | 10/2012 | Nusbaum | A63B 69/36 473/278 |
| 8,460,111 | B2 * | 6/2013 | Hart | A63B 24/0003 463/42 |
| 8,803,913 | B1 * | 8/2014 | Edmonston | G06T 7/20 345/629 |
| 8,903,521 | B2 * | 12/2014 | Goree | A61B 5/1118 700/90 |
| 9,697,613 | B2 * | 7/2017 | Tofolo | G06T 7/20 |
| 2002/0019276 | A1 * | 2/2002 | Kuta | A63B 24/0021 473/405 |
| 2002/0082122 | A1 * | 6/2002 | Pippin | A63B 57/00 473/407 |
| 2004/0032970 | A1 | 2/2004 | Kiraly et al. | |
| 2005/0012023 | A1 | 1/2005 | Vock et al. | |
| 2005/0285877 | A1 * | 12/2005 | Dengler | G06T 7/97 345/632 |
| 2006/0008116 | A1 * | 1/2006 | Kiraly | G06T 7/20 382/103 |
| 2006/0189398 | A1 * | 8/2006 | Zanzucchi | A63B 24/0003 473/151 |
| 2007/0298896 | A1 * | 12/2007 | Nusbaum | A63B 69/36 473/131 |
| 2008/0254916 | A1 | 10/2008 | Kim et al. | |
| 2009/0082139 | A1 * | 3/2009 | Hart | A63B 24/0003 473/407 |
| 2011/0230985 | A1 | 9/2011 | Niegowski et al. | |
| 2011/0237344 | A1 * | 9/2011 | Nusbaum | A63B 69/36 473/278 |
| 2012/0057150 | A1 | 3/2012 | Hess et al. | |
| 2012/0116548 | A1 * | 5/2012 | Goree | A61B 5/1118 700/90 |
| 2012/0251079 | A1 | 10/2012 | Meschter et al. | |
| 2014/0277635 | A1 | 9/2014 | Thurman et al. | |
| 2014/0300733 | A1 | 10/2014 | Mitchell et al. | |
| 2015/0154452 | A1 * | 6/2015 | Bentley | G06K 9/00711 386/201 |
| 2015/0317801 | A1 * | 11/2015 | Bentley | H04N 7/181 382/107 |
| 2016/0184698 | A1 * | 6/2016 | Tan | A63F 13/216 463/2 |
| 2016/0350922 | A1 * | 12/2016 | Tofolo | G06T 7/20 |
| 2017/0350960 | A1 * | 12/2017 | McCarthy | G01S 5/0294 |

* cited by examiner

PORTABLE SYSTEM FOR OBTAINING SPORTS INFORMATION

BACKGROUND

The importance of data analytics continues to grow with respect to sports. With greater access to information comes greater understanding of the particular sport. Some sports, such as baseball, have heavily developed datasets and accompanying data analytics. Other sports, such as tennis, are still developing in terms of a data collection and analysis. Because of the nuanced nature of the sport, tennis does not provide a rich dataset that is easily ascertainable by a spectator. In order to obtain detailed statistics such as serve speed, ball placement, ball trajectory, player movement, and other similar aspects, expensive equipment is typically required.

While expensive equipment may be available for professional players, these systems are unavailable to the vast majority of tennis players. For example, current "home" systems for tennis analytics require multiple (typically six) high-definition cameras mounted on permanent mounts and connected to a standalone computer (typically a kiosk) that is located near the court. Beyond the cost, this system has the obvious drawback of lacking portability. The system, once installed, can only be used on that particular court. If a player chooses to practice at a different court, the system is entirely useless.

On the other end of the analytics spectrum exist applications for use on a smartphone, tablet, laptop, or other handheld computer device (collectively referred to herein as a "mobile device") that provide basic measurements of sports data. These systems are severely limited in their abilities. For example, with respect to applications that measure tennis serve speed, many rely on a user to manually press a button when the serve begins and ends. In a sport where the ball routinely travels at over 100 mph, relying on a human to manually indicate a start and end of a serve is simply not accurate enough to be useful. Another drawback of these types of systems is the requirement of manually inputting the location at which the ball bounces on the court. Yet another drawback is the need to manually input the distance between the mobile device and the service location of the ball. After all these manual inputs, most mobile-device based systems merely provide an estimate of serve speed. More detailed analytics are simply unavailable on a mobile-device based system at this point in time.

For at least these reasons, a need exists for a cost-effective, portable system that obtains and analyzes detailed sports information. The present disclosure provides a solution focusing primarily on the sport of tennis, but is also applicable to other sports. The solution is cost effective and portable, potentially using only a mobile device while providing a wide variety of statistics and data.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

SUMMARY

The following summary of the invention provides a basic understanding of some aspects of various embodiments of the present disclosure through the use of example embodiments. This summary is intended to supplement, and be read in conjunction with, at least the detailed description, claims, and drawings.

In one example embodiment, a method is provided for obtaining information on a ball in flight using a mobile device. The example method includes calculating a distance between the mobile device and a launch point of the ball; recording, via a camera of the mobile device, a video of the flight of the ball; analyzing the video to determine at least one flight characteristic; and determining, based on the at least one flight characteristic, an average speed of the ball during flight. Further, analyzing the video to determine at least one flight characteristic may also include determining a launch frame of the video at which the ball was launched; determining a landing frame of the video at which the ball landed; determining, based on a framerate of the video, a number of intervening frames between the launch frame and the landing frame of the video; and calculating an average speed of the ball during flight based on the number of intervening frames.

In another example embodiment, calculating a distance may be done utilizing a geographic map associated with a geographic location of the ball and/or mobile device. For example, the mobile device may access a map that provides information regarding the location of a tennis court in relation to the mobile device.

In some embodiments, analyzing the video may further comprise, for example, locating the ball within the video; measuring a size of the ball in the video; and measuring the rate of change of the size of the ball during flight. This embodiment may also include determining an average speed of the ball by calculating the rate of change of the size of the ball and using that information to determine average speed.

Other example embodiments relate to displaying information relating to the ball and/or player(s). For example, a display may depict, on a user interface, a graphic depicting the flight path of the ball relative to the court. As another example, the flight path of the ball may be displayed in such a way as to indicate the average speed of the ball—for example, via color, line type, line thickness, and so on. The display may also show, for example, a direction and/or magnitude of ball spin using colors, arrows, or other display elements.

In another example embodiment, a system is provided for tracking sports activity within a playing area. The embodiment may include, for example, a mobile device having a camera; a sensor configured to be worn by a player of the sports activity and configured to wirelessly communicate with the mobile device. The mobile device may track movement of the ball by processing data received by the camera. The mobile device may also track player movement via information received from the sensor worn by the player. Additionally, the mobile device can be configured to display a graphical representation of the ball and/or player movement within the playing area.

In one example embodiment, the sensor worn by a player can determine a player position using a Global Positioning System (GPS) module that detects the sensors global location at a particular point in time. The mobile device can receive the GPS location of the sensor and, for example, compare it to the GPS location of the mobile device in order to determine a distance between the two. In another example embodiment the sensor may emit a light detectable by the mobile device, via a camera, and the mobile device can calculate player position based on the estimated location of that light. The mobile device may use information received from, or based on, the sensor to calculate at least one of average player movement speed, maximum player movement speed, and/or player reaction time.

Sensors may be used in other ways as well. For example, and impact sensor may be worn by the user or placed on a striking instrument such a tennis racket. The impact sensor can detect inertial changes that indicate impact between the racket and the ball. The sensor can then send this information to the mobile device, providing the mobile device with information sufficient to determine an accurate estimate of the time and/or location of the ball strike.

Additional features and advantages of the invention will be made apparent from the following detailed description of illustrative embodiments that proceeds with reference to the accompanying drawings.

BRIEF DESCRIPTION OF THE DRAWINGS

The following detailed description will be better understood when read in conjunction with the appended drawings, in which there is shown one or more of the multiple embodiments of the present invention. It should be understood, however, that the various embodiments of the present invention are not limited to the precise arrangements and instrumentalities shown in the drawings.

DETAILED DESCRIPTION

A cost-effective, portable system is provided for obtaining and analyzing detailed sports information. The system may include, for example, a mobile device capable of calculating a distance between itself and a launch point of a ball, recording a video of the flight of the ball, analyzing the video to determine at least one flight characteristic, and determining, based on the at least one flight characteristic, an average speed of the ball during flight. The system may also include a sensor worn by a player and configured to wirelessly transmit various types of information to the mobile device for further processing.

Figure 1:
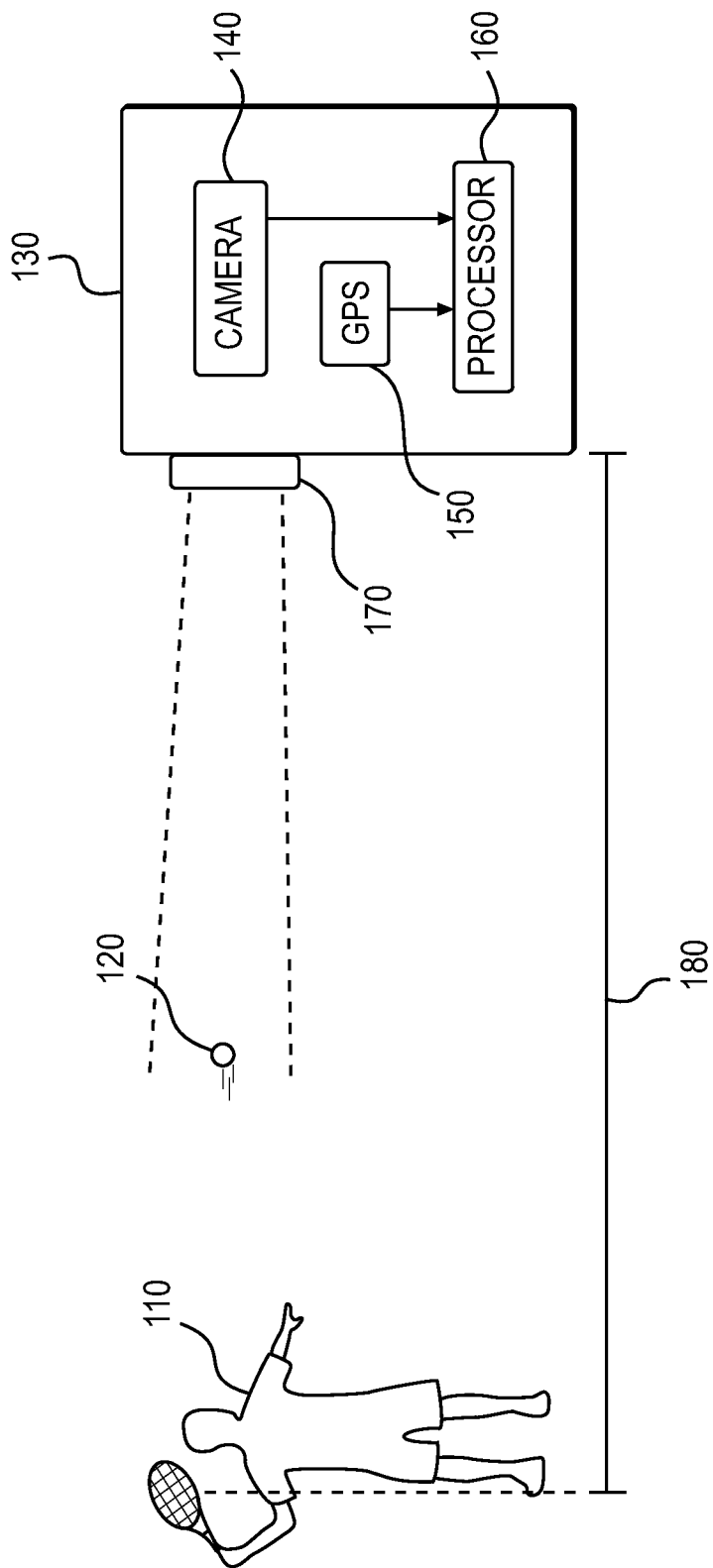
FIG. 1 is a representative schematic depicting an example embodiment of a system for obtaining information on a ball in flight.

FIG. 1 is a representative schematic depicting an example embodiment of a system for obtaining information on a ball in flight. FIG. 1 shows a player 110 striking a tennis ball 120 in the general direction of a mobile device 130. While this example is based on the sport of tennis, the embodiment is equally applicable to any sport that involves propelling a ball or other object. Further, the mobile device 130 is depicted in an abstract manner intended to show details of the device, and is not intended to be drawn to scale.

The mobile device 130 includes at least a camera 140, GPS unit 150, and a processor 160. The camera 140 may be configured to operate a lens 170 pointed toward the ball 120 and player 110. The lens 170 focuses on the ball 120 and follows its path through the air, preferably until the ball 120 contacts the ground or another object. Via the lens 170, the camera 140 obtains visual information about the ball 120 and sends the information to the processor 160. That information may contain a variety of data about the ball 120, such as the size of the ball 120 in each particular frame, the rate of change of the size of the ball 120 from frame to frame, and so on. The processor 160 receives this information and uses it to perform various calculations.

Additionally, processor 160 receives location information from GPS unit 150. At a minimum, the GPS unit 150 provides information to the processor 160 regarding the location of the mobile device 130. In some embodiments, the GPS unit 150 receives location information from additional sources and provides that information to the processor 160. For example, the GPS unit 150 may store information about a previous location of the mobile device 130. This may be useful where a user marks the location of the player 110 prior to the player serving the ball 120, by walking to that spot and instructing the mobile device 130 to save that location. Then, when the mobile device 130 is in a location spaced apart from the player 110, the new GPS location provides an accurate measure of distance 180 between the player 110 and the mobile device 130.

The mobile device 130 may calculate distance 180 using other methods as well. For example, the GPS unit 150 may indicate to the processor 160 that the mobile device 130 is located near a tennis court. Meanwhile, the camera 140 may indicate to the processor 160 that the player 110 is standing on the baseline of a particular side of the tennis court. Using this information, the processor 160 may calculate a distance 180 between the player 110 and the mobile device 130.

Figure 2:
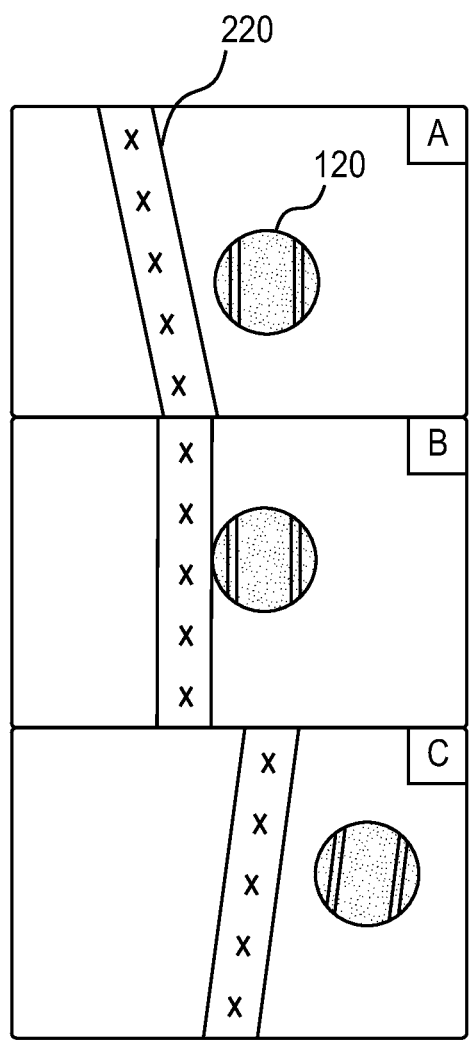
FIG. 2 is a schematic depicting three example frames in a recorded video used to obtain information on a ball in flight.

In order to calculate more precise information about a ball in flight, the mobile device may parse individual frames to determine various things. FIG. 2, for example, is an illustration of three frames (A, B, and C, respectively) captured by the camera of a mobile device. Each frame shows a tennis ball 120 relative to a tennis racket 220 before, during, and after a strike of the ball 120. In frame A, the racket 220 is approaching but has not yet struck the ball 120. In frame B, the racket 220 is in the process of striking the ball 120. Finally, in frame C, the ball 120 has left the racket 220. The processor of the mobile device is able to analyze these frames to determine a launch point of the ball 120; in this case, the launch point corresponds to frame B. The processor is able to correlate a particular frame with a particular point in time, and use this to calculate the flight time of the ball 120.

A similar frame-by-frame determination is performed at the other end of the ball's flight, where the ball impacts the ground or another object such as the net, another player's racket, or in unfortunate cases, the body of another player. This determination provides a definitive start and end to the ball's flight through the air, framing further calculations such as average speed, spin direction, spin rate, distance covered, and so on. For example, the processor is aware of the particular framerate used to record the flight of the ball, and is aware of the number of frames elapsed during the ball's flight. Based on these values, the processor is able to calculate the time elapsed during the ball's flight.

Figure 3:
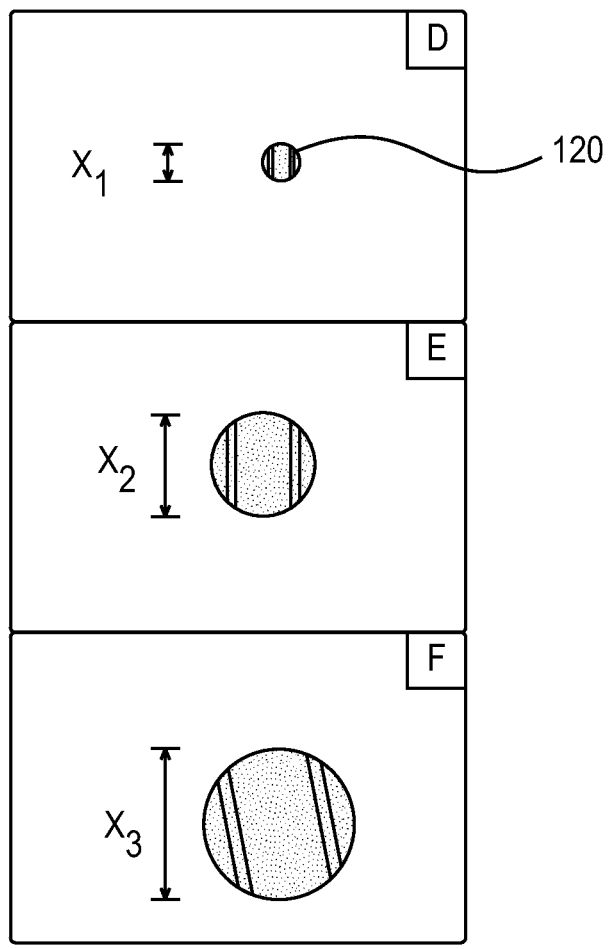
FIG. 3 is a schematic depicting three example frames in a recorded video used to obtain information on a ball in flight.

With respect to determining distance, the processor is configured to calculate this based on frame information as well. As shown in FIG. 3, for example, the size of the ball 120 changes as its distance from the camera changes. The three frames shown in FIG. 3. (D, E, and F) capture the ball 120 at three locations that are progressively closer to the camera. The processor measures the size of the ball in each frame relative to the overall frame size. The size of the ball in frame D is shown as $X_1$, the size of the ball in frame E is shown as $X_2$, and the size of the ball in frame F is shown as $X_3$. In addition to these measurements, the processor can use a measurement of the size of the ball at its launch point as well as the known size of the ball (in this case, the known size of a tennis ball). Based on these various pieces of information, the processor is able to determine the distance traveled between any two frames. And because the processor is aware of the framerate, it can also determine the time traveled between any two frames. These two pieces of information—time and distance—provide the data necessary to calculate ball speed.

The speed of the ball may be calculated in a variety of ways. For example, the processor may use the calculated overall distance traveled and overall time to determine an average speed. Alternatively, the processor can break the ball's flight into various subparts and calculate the average speed and distance traveled for each of those subparts. This alternative example may be used in addition to using the overall distance and time calculations, and may be used to improve or otherwise modify those calculations. By using multiple types of calculations, the estimates of ball speed and distance traveled can be cross-checked and improved. The processor may adapt to a particular environment (e.g., low light, non-ideal background) based on cross validation from its various calculations regarding at least speed and distance.

Figure 4:
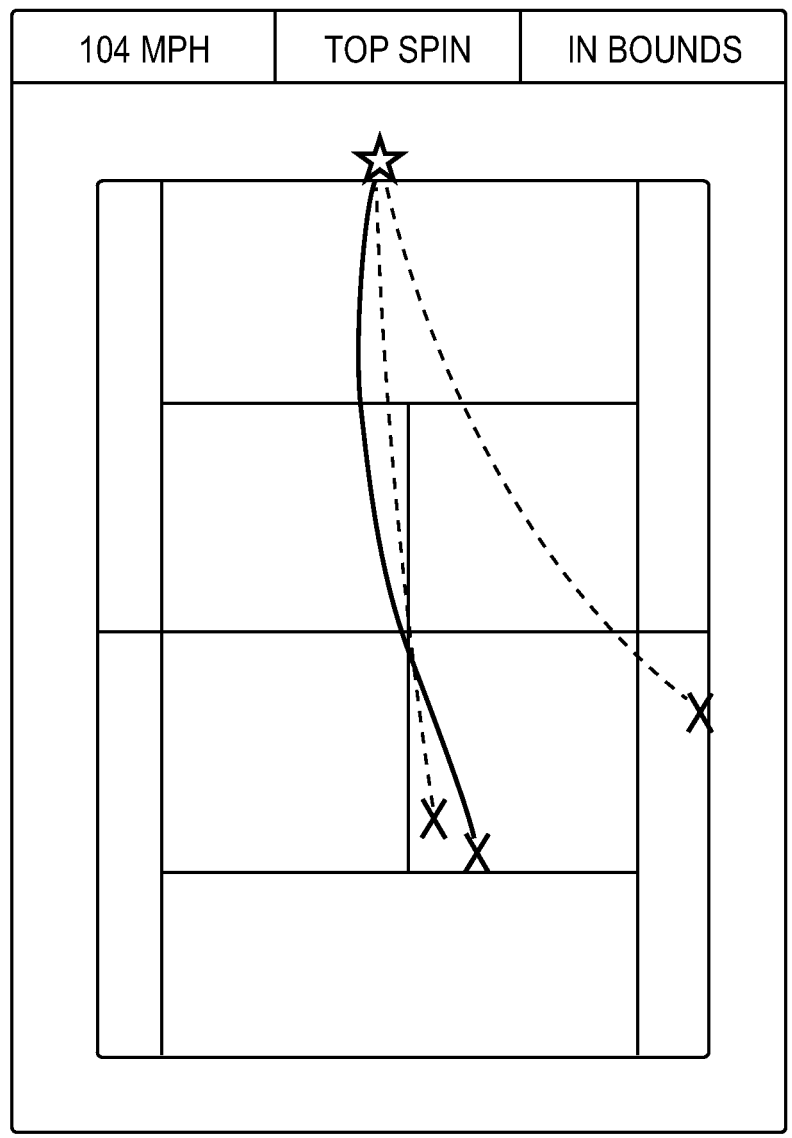
FIG. 4 is a representative illustration of a display showing information relating to the trajectory of a tennis ball relative to a tennis court.

In addition to performing the various calculations explained above, the mobile device may be configured to graphically represent different types of information on the display of the mobile device. For example, FIG. 4 shows a representative illustration of a display showing information relating to the trajectory of a tennis ball relative to a tennis court. The star on the display represents the player's service location, while the X's mark the point on the court where the ball first contacts the court. In this example, the solid line represents the most recent serve while the dashed lines represent previous serves. Also, information regarding the most recent serve is provided along the top of the display. In this example, that information includes the average velocity of the ball, the spin direction, and whether the ball landed inside or outside the boundaries of play.

In some embodiments, the display may use color coding to provide more information to the user without cluttering the user interface. For example, the trajectory of the serve may be displayed in a color corresponding to the average speed of the serve. The colors may be calibrated to the particular player, such that a serve considered quite fast for that particular player is shown in red, while a serve considered quite slow for that particular player is shown in blue. Intermediate speeds may be shown in intermediate colors. For example, the user may indicate that a serve over 110 mph is fast enough to be shown in red for that player, while a serve over 100 mph should be orange, a server over 90 mph should be yellow, and so on. Alternatively, the mobile device may have predetermined settings based on the player's age, size, sex, skill level, and any other factors that may affect serve speed (e.g., weather).

Figure 5:
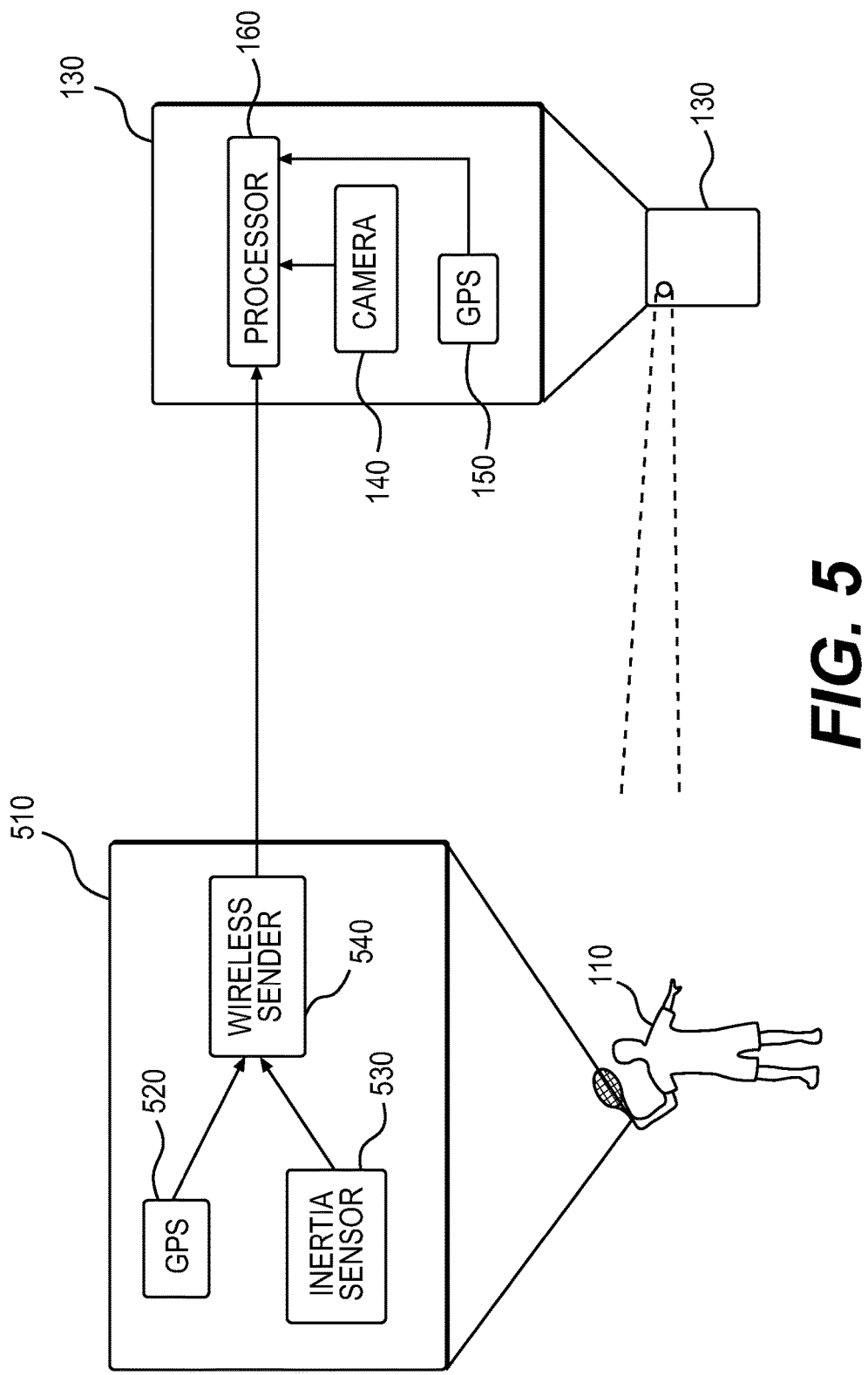
FIG. 5 is a representative diagram illustrating an example system for obtaining information on a ball in flight as well as a player.

While the mobile device described herein is capable of calculating and tracking numerous characteristics of the ball without using any other external devices, it is possible to incorporate such devices in order to improve accuracy or provide more information. For example, one or more external sensors may be deployed such that they communicate additional information to the mobile device. FIG. 5 shows an example representation of a sensor 510 located on a player 110. The sensor 510 may be worn by the player 110 or may be attached to the player's racket. The sensor 510 can include a variety of components. As shown in FIG. 5, it may contain a GPS unit 520 and/or an inertia sensor 530. Both of these units can communicate with the processor 160 of the mobile device 130 via a wireless sending unit 540. Any known type of wireless communication, such as Bluetooth or WiFi, may be used.

The GPS unit 520 can obtain location information relating to the player. This location information provides the processor 160 of the mobile device 130 with precise information regarding the launch point of the ball. The processor 160 is therefore able to more accurate judge the distance traveled by the ball, and accordingly, the average velocity of the ball. The inertia sensor 530 can be configured such that it senses when a player's racket strikes the ball. The vibrations and/or forces experienced by the inertia sensor 530 can indicate the precise moment that the ball is contacted by the player 110. This information can then be sent to the processor 160 of the mobile device 130, further increasing the accuracy of the calculations.

Figure 6:
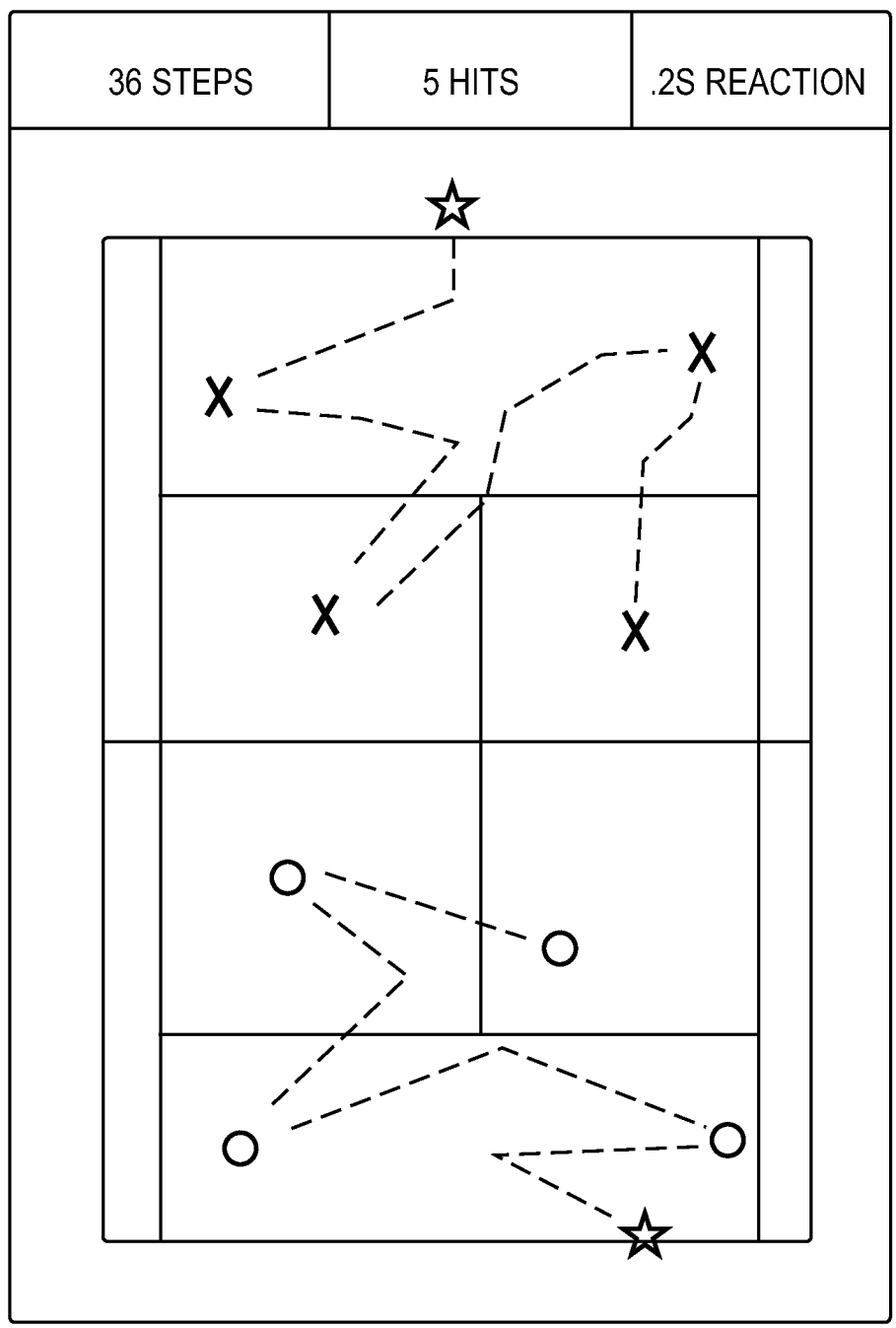
FIG. 6 is a representative illustration of a display showing information relating to the actions of two players relative to a tennis court.

Player-worn sensors can be used in conjunction with the display of the mobile device to provide detailed information regarding player movement, strike location, and other statistics. For example, FIG. 6 depicts an example display of a mobile device showing information relating to the actions of two players relative to a tennis court. In this example embodiment, each player is wearing a sensor communicating with the mobile device. The display shows information regarding each player's initial strike location (shown as a star for each player) as well as each player's subsequent strikes (shown X's and O's, respectively). The display also shows the paths traveled by each player between each strike. The display can also be configured to show additional information such as the number of steps taken by either player, the number of hits by either player, and a player's reaction time (for example, the amount of time elapsed between the launch point of a serve and the player's first substantial movement).

The information presented on the display may be coded to show a variety of different factors. For example, the line between each strike location may be presented in a particular color, or a particular line thickness/type, corresponding to the player's movement speed. Additionally, for example, each strike location may be presented in a size and/or color corresponding to the velocity of that particular strike. A winning shot may be shown larger, or in a different color. In other embodiments, a heat map can be created showing the locations on the court most frequently traveled by each player. A similar shot map could be created, showing the totality of all shots, or all winning shots, by each player and their particular locations on the court. Other variations may be incorporated into the display and presented to a user for further customization.

Those skilled in the art will recognize that the program instructions for software applications implementing all or a portion of one or more embodiment(s) of the present disclosure may be written in a programming language such as Java or C++, and that the database may be implemented with a database package such as Microsoft Access™ or a database management system (DBMS) such as Microsoft SQL Server™, Microsoft SQL Server CE™, IBM DB2™, MySQL, or postgreSQL.

The embodiments of the present disclosure can be included in an article of manufacture (e.g., one or more computer program products) having, for instance, computer useable or computer readable media. The media has embodied therein, for instance, computer readable program code means, including computer-executable instructions, for providing and facilitating the mechanisms of the embodiments of the present disclosure. The article of manufacture can be included as part of a computer system or sold separately.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of the present disclosure is not limited to the particular examples and implementations disclosed herein, but is intended to cover modifications within the spirit and scope thereof as defined by the appended claims and any and all equivalents thereof.

What is claimed is:

1. A method of obtaining information on a ball in flight using a mobile device comprising at least a camera and a processor, said method comprising:

calculating, by the processor, a distance between the mobile device and a launch point of the ball;

recording, via the camera of the mobile device, a video of the flight of the ball;

analyzing, by the processor, the video to determine at least one flight characteristic; and determining, by the processor, based on the at least one flight characteristic, an average speed of the ball during flight, wherein analyzing the video to determine at least one flight characteristic further comprises:

determining from the video, by the processor, a launch frame of the video at which the ball was launched;

determining from the video, by the processor, a landing frame of the video at which the ball landed;

determining, by the processor, based on a framerate of the video, a number of intervening frames between the launch frame and the landing frame of the video;

calculating, by the processor, an average speed of the ball during flight between the launch frame and the landing frame of the video based on the number of intervening frame;

determining from the video, by the processor, a beginning subset frame of the intervening frames;

determining from the video, by the processor, and ending subset frame of the intervening frames;

determining from the video, by the processor, any consecutive frames from the video existing between the beginning subset frame and the ending subset frame, wherein the beginning subset frame, the consecutive frames between the beginning subset frame and the ending subset frame, and the ending subset frame comprise a subset of frames, said subset of frames a part of but less than the number of intervening frames and said subset of frames captured during a subset of the flight of the ball between the launch frame and the ending frame;

measuring, by the processor, a rate of change of a size of an image of the ball during the subset of flight of the ball by locating and analyzing the image of the ball in two or more frames of the subset of frames;

determining, by the processor, a subset average speed of the ball during the subset of the flight of the ball based on a known size of the ball and the rate of change of the size of the image of the ball during the subset of flight; and revising, by the processor, the average speed of the ball during flight between the launch frame and the landing frame of the video using the subset average speed of the ball during the subset of the flight of the ball.

2. The method of claim 1, wherein calculating a distance further comprises the processor utilizing a Global Positioning System module.

3. The method of claim 1, wherein calculating a distance further comprises the processor utilizing a geographic map associated with a geographic location of the ball and/or mobile device.

4. The method of claim 1, further comprising the processor tracking a flight path of the ball and displaying, on a user interface, a graphic depicting the flight path of the ball.

5. The method of claim 4, wherein the graphic depicting the flight path of the ball is color coded according to the average speed of the ball flight.

6. The method of claim 4, further comprising the processor calculating, based on the calculated average speed and the tracked flight path of the ball, a direction and/or a magnitude of ball spin.

7. The method of claim 6, wherein the graphic depicting the flight path of the ball is color coded according to the direction and/or magnitude of ball spin.

8. A system for tracking sports activity within a playing area, comprising:

a mobile device comprising at least a camera and a processor; and a sensor configured to be worn by a player of the sports activity, the sensor configured to wirelessly communicate with the mobile device;

wherein the mobile device tracks movement of the ball by the processor processing data received by the camera;

wherein the mobile device tracks player movement via information received by the processor from the sensor worn by the player; and wherein the mobile device is configured to display a graphical representation of the ball and/or player movement within the playing area, wherein the mobile device tracking movement of the ball by the processor processing data received by the camera further comprises:

determining from a video captured by the camera, by the processor, a launch frame of the video at which the ball was launched;

calculating, by the processor, a distance between the mobile device and the launch point of the ball;

determining from the video, by the processor, a landing frame of the video at which the ball landed;

determining, by the processor, based on a framerate of the video, a number of intervening frames between the launch frame and the landing frame of the video;

calculating, by the processor, an average speed of the ball during flight between the launch frame and the landing frame of the video based on the number of intervening frames;

determining from the video, by the processor, a beginning subset frame of the intervening frames;

determining from the video, by the processor, and ending subset frame of the intervening frames;

determining from the video, by the processor, any consecutive frames from the video existing between the beginning subset frame and the ending subset frame, wherein the beginning subset frame, the consecutive frames between the beginning subset frame and the ending subset frame, and the ending subset frame comprise a subset of frames, said subset of frames a part of but less than the number of intervening frames and said subset of frames captured during a subset of the flight of the ball between the launch frame and the ending frame;

measuring, by the processor, a rate of change of a size of an image of the ball during the subset of flight of the ball by locating and analyzing the image of the ball in two or more frames of the subset of frames;

determining, by the processor, a subset average speed of the ball during the subset of the flight of the ball based on a known size of the ball and the rate of change of the size of the image of the ball during the subset of flight; and revising, by the processor, the average speed of the ball during flight between the launch frame and the landing frame of the video using the subset average speed of the ball during the subset of the flight of the ball.

9. The system of 8, wherein the sensor is configured to determine a player position via a GPS module.

10. The system of 9, wherein the mobile device comprises a GPS module and is configured to measure a distance between the mobile device and the player by the processor comparing the GPS locations of the mobile device and the sensor.

11. The system of 8, wherein the sensor emits a light detectable by the mobile device.

12. The system of 11, wherein the processor of the mobile device calculates player position based on the location of the emitted light.

13. The system of 8, wherein the mobile device calculates, by the processor, at least one of average player movement speed, maximum player movement speed, and/or player reaction time.

14. The system of 8, further comprising an impact sensor configured to be worn by the user and/or placed on a striking instrument, wherein the impact sensor detects the time of impact with the ball.

15. The system of 14, wherein the processor of the mobile device calculates ball speed based, at least in part, on information received from the impact sensor regarding the time of impact with the ball.

* * * * *